(12) United States Patent
Shima et al.

(10) Patent No.: US 9,237,904 B2
(45) Date of Patent: Jan. 19, 2016

(54) PUNCTURING INSTRUMENT

(75) Inventors: Takumi Shima, Ehime (JP); Akio Nagao, Kagawa (JP)

(73) Assignee: PANASONIC HEALTHCARE HOLDINGS CO., LTD., Tokyo (JP)

(*) Notice: Subject to any disclaimer, the term of this patent is extended or adjusted under 35 U.S.C. 154(b) by 260 days.

(21) Appl. No.: 13/991,014

(22) PCT Filed: Dec. 5, 2011

(86) PCT No.: PCT/JP2011/006795
§ 371 (c)(1),
(2), (4) Date: May 31, 2013

(87) PCT Pub. No.: WO2012/077328
PCT Pub. Date: Jun. 14, 2012

(65) Prior Publication Data
US 2013/0253560 A1    Sep. 26, 2013

(30) Foreign Application Priority Data
Dec. 6, 2010  (JP) .................. 2010-271045

(51) Int. Cl.
*A61B 17/34* (2006.01)
*A61B 5/15* (2006.01)
*A61B 5/151* (2006.01)

(52) U.S. Cl.
CPC .............. *A61B 17/34* (2013.01); *A61B 5/1411* (2013.01); *A61B 5/1519* (2013.01);
(Continued)

(58) Field of Classification Search
CPC ........... A61B 5/14532; A61B 5/15186; A61B 5/15148; A61B 5/15022; A61B 5/1411; A61B 5/15115; A61B 5/15109; A61B 5/15107; A61B 5/15192; A61B 5/15188; A61B 5/15194; A61B 5/1519

USPC ................................ 606/181, 185
See application file for complete search history.

(56) References Cited

U.S. PATENT DOCUMENTS 4,442,836 A   4/1984   Meinecke et al.
6,929,649 B2  8/2005   Pugh
(Continued)

FOREIGN PATENT DOCUMENTS

| CN | 1981702 | 6/2007 |
|---|---|---|
| CN | 101166466 | 4/2008 |

(Continued)

OTHER PUBLICATIONS

International Preliminary Report on Patentability and Written Opinion of the International Searching Authority issued Jun. 20, 2013 in International (PCT) Application No. PCT/JP2011/006795.
(Continued)

*Primary Examiner* — Jonathan W Miles
*Assistant Examiner* — George J Ulsh
(74) *Attorney, Agent, or Firm* — Wenderoth, Lind & Ponack, L.L.P.

(57) ABSTRACT

A puncturing instrument includes a cylindrical main body case having a puncture aperture on a lower end side; a needle holder provided on a puncture aperture side inside the cylindrical main body case; a first elastic object for moving the needle holder to the puncture aperture side; and a second elastic object for pulling the needle holder back to an upper end side inside the cylindrical main body case, from a state in which the needle holder is moved to the puncture aperture side by the first elastic object. A rotator rotates around a rotation shaft fixed to the cylindrical main body case, and is coupled with a coupling portion of the needle holder on a first one of two sides of the rotator with the rotation shaft interposed therebetween and is coupled with the second elastic object on a second one of the two sides of the rotator.

15 Claims, 25 Drawing Sheets

(52) U.S. Cl.
CPC ...... *A61B 5/150022* (2013.01); *A61B 5/15107* (2013.01); *A61B 5/15117* (2013.01); *A61B 5/15194* (2013.01); *A61B 5/150412* (2013.01); *A61B 5/150519* (2013.01); *A61B 5/150549* (2013.01); *A61B 5/150717* (2013.01); *A61B 5/150183* (2013.01)

(56) References Cited

U.S. PATENT DOCUMENTS

| | | |
|---|---|---|
| 2007/0100256 A1 | 5/2007 | Sansom |
| 2007/0260272 A1 | 11/2007 | Weiss et al. |
| 2009/0198265 A1 | 8/2009 | Ono et al. |

FOREIGN PATENT DOCUMENTS

| | | |
|---|---|---|
| JP | 2002-85384 | 3/2002 |
| JP | 2007-125383 | 5/2007 |
| JP | 2007-301361 | 11/2007 |
| JP | 2010-94403 | 4/2010 |

OTHER PUBLICATIONS

Office Action issued Jun. 26, 2014 in Chinese Application No. 201180058726.5, with partial English translation.
International Search Report issued Dec. 27, 2011 in International (PCT) Application No. PCT/JP2011/006795.

PUNCTURING INSTRUMENT

CROSS REFERENCE TO RELATED APPLICATION

This application claims the benefit of Japanese Patent Application No. 2010-271045 filed on Dec. 6, 2010 in Japan, the contents of which are incorporated herein by reference.

FIELD OF THE INVENTION

The invention relates to a puncture instrument for puncturing a human body to allow the blood to flow out, for example, in order to measure the blood sugar level.

BACKGROUND OF THE INVENTION

The configuration of such a puncture instrument would conventionally be as follows.

That is, it would comprise: a cylindrical main body case having a puncture aperture on the lower end side; a needle holder provided on the puncture aperture side inside the main body case; a first elastic object for moving the needle holder to the puncture aperture side; and a second elastic object for pulling the needle holder, moved to the puncture aperture side by the first elastic object, back to the upper end side inside the main body case (e.g. Patent document 1).

[Patent document 1] Japanese Patent Laid-Open Application No. 2002-085384

Problems to be Solved by the Invention

When the puncture is performed with the above-described conventional puncture instrument, the first elastic object rapidly moves the needle holder to the lower end side of the main body case, allowing a puncture needle to puncture a human body. The puncture needle is pulled back into the main body case by the first elastic object returning immediately after the puncture, but the first elastic object may repeat the extension and contraction, causing the puncture needle to protrude again toward the human body. The second elastic object is thus provided to prevent the puncture needle from protruding again, and its elasticity inhibits the repeated protrusion of the puncture needle.

However, the puncture needle may still protrude again in spite of such placement of the second elastic object, and therefore a repeated protrusion prevention mechanism is placed to prevent this repeated protrusion of the puncture needle. The repeated protrusion prevention mechanism is provided with, for example, an impact wall to be hit by the needle holder holding the puncture needle that is going to protrude again, and the provision of this impact wall would indeed prevent the repeated protrusion of the puncture needle.

The impact with such an impact wall, however, creates a large impact sound, which is very obstructive to a puncturing person as an abnormal sound during puncture, and this abnormal sound is required to be inhibited.

SUMMARY OF THE INVENTION

A purpose of the invention is thus to inhibit the abnormal sound during puncture.

Means for Solving the Problems

In order to achieve this objective, the invention comprises: a cylindrical main body case having a puncture aperture on the lower end side; a needle holder provided on the puncture aperture side inside the main body case; a first elastic object for moving the needle holder to the puncture aperture side; and a second elastic object for pulling the needle holder, moved to the puncture aperture side by the first elastic object, back to the upper end side inside the main body case, where a rotator which rotates around a rotation shaft fixed to the main body case is provided above a needle holding portion of the needle holder inside the main body case, and where the rotator is coupled with a coupling portion of the needle holder on one of both sides of the rotator with the rotation shaft interposed therebetween and is coupled with the second elastic object on the other side. This allows the intended objective to be achieved.

Advantages of the Invention

The invention is provided with the second elastic object for pulling the needle holder, moved to the puncture aperture side by the first elastic object, back to the upper end side inside the main body case, where the rotator which rotates around the rotation shaft fixed to the main body case is provided above the needle holding portion of the needle holder inside the main body case, and where the rotator is coupled with the coupling portion of the needle holder on one of both sides of the rotator with the rotation shaft interposed therebetween and is coupled with the second elastic object on the other side. The repeated protrusion of the puncture needle is therefore prevented by the rotation of the rotator, which means that no impact sound is created unlike those which are provided with a conventional impact wall. As a result, the generation of an abnormal sound during puncture can be inhibited.

There are other aspects of the invention as described below. This disclosure of the invention therefore intends to provide part of the aspects of the invention and does not intend to limit the scope of the invention described and claimed herein.

DETAILED DESCRIPTION OF EMBODIMENTS

The following is a detailed description of the invention. The embodiment described below is only an example of the invention, and the invention can be varied in various aspects. Therefore, the specific configurations and functions disclosed below do not limit the claims.

Figure 1:
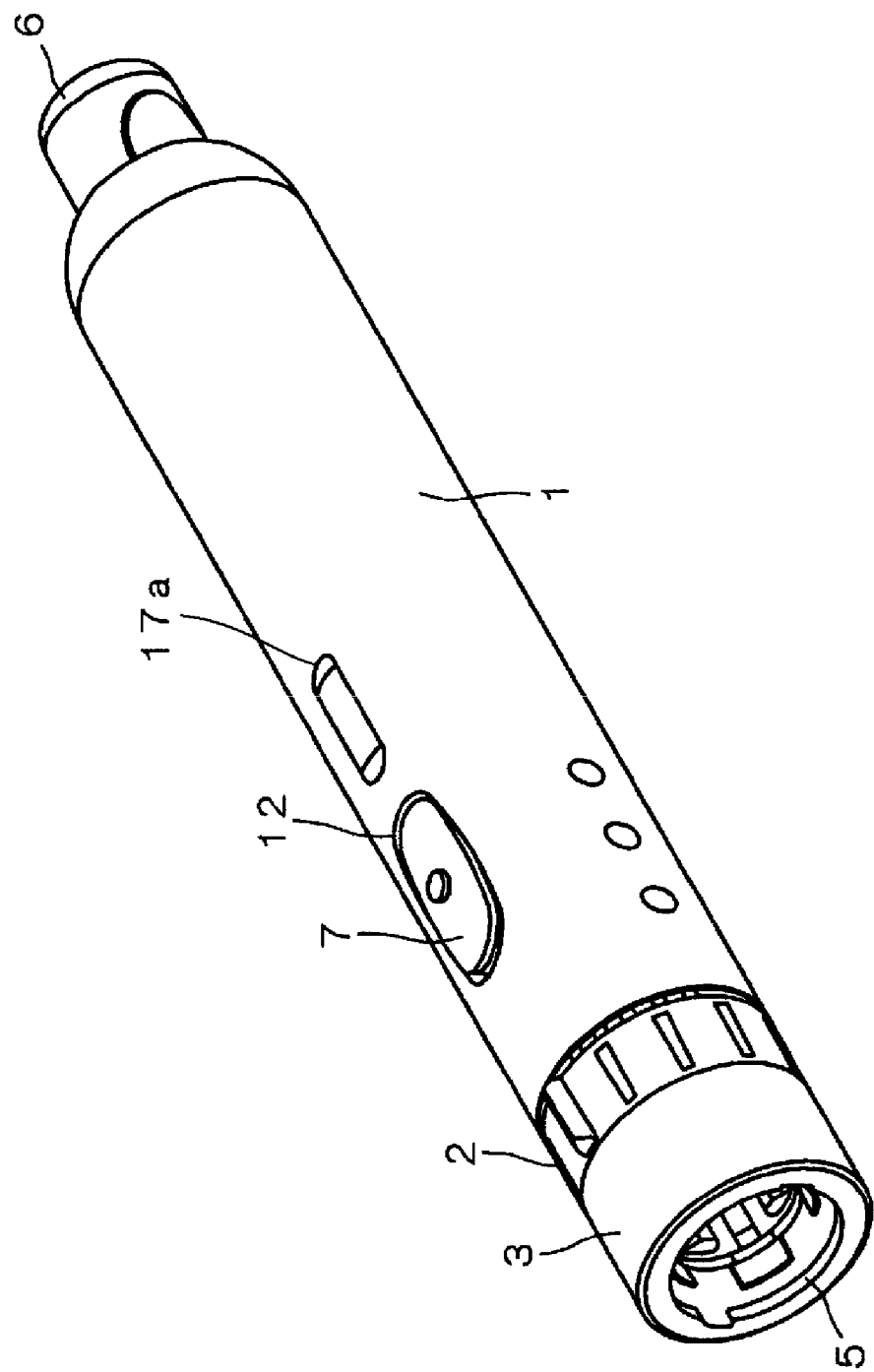
FIG. 1 is a perspective view of a puncture instrument according to one embodiment of the invention.

In FIG. 1, a puncture instrument according to an embodiment comprises a cylindrical main body case 1, near an opening on the lower end side of which are attached a puncture depth adjustment ring 2 and a front-end ring 3. The adjustment ring 2 and the front-end ring 3 are shown in detail in FIG. 2. The puncture depth adjustment ring 2 here, as is well known, is rotated to adjust the puncture depth of a puncture needle 4 (see FIG. 13). The front-end ring 3 is located below the puncture depth adjustment ring 2 on the lower end side, and an opening of this front-end ring 3 constitutes a puncture aperture 5 of the main body case 1.

Figure 2:
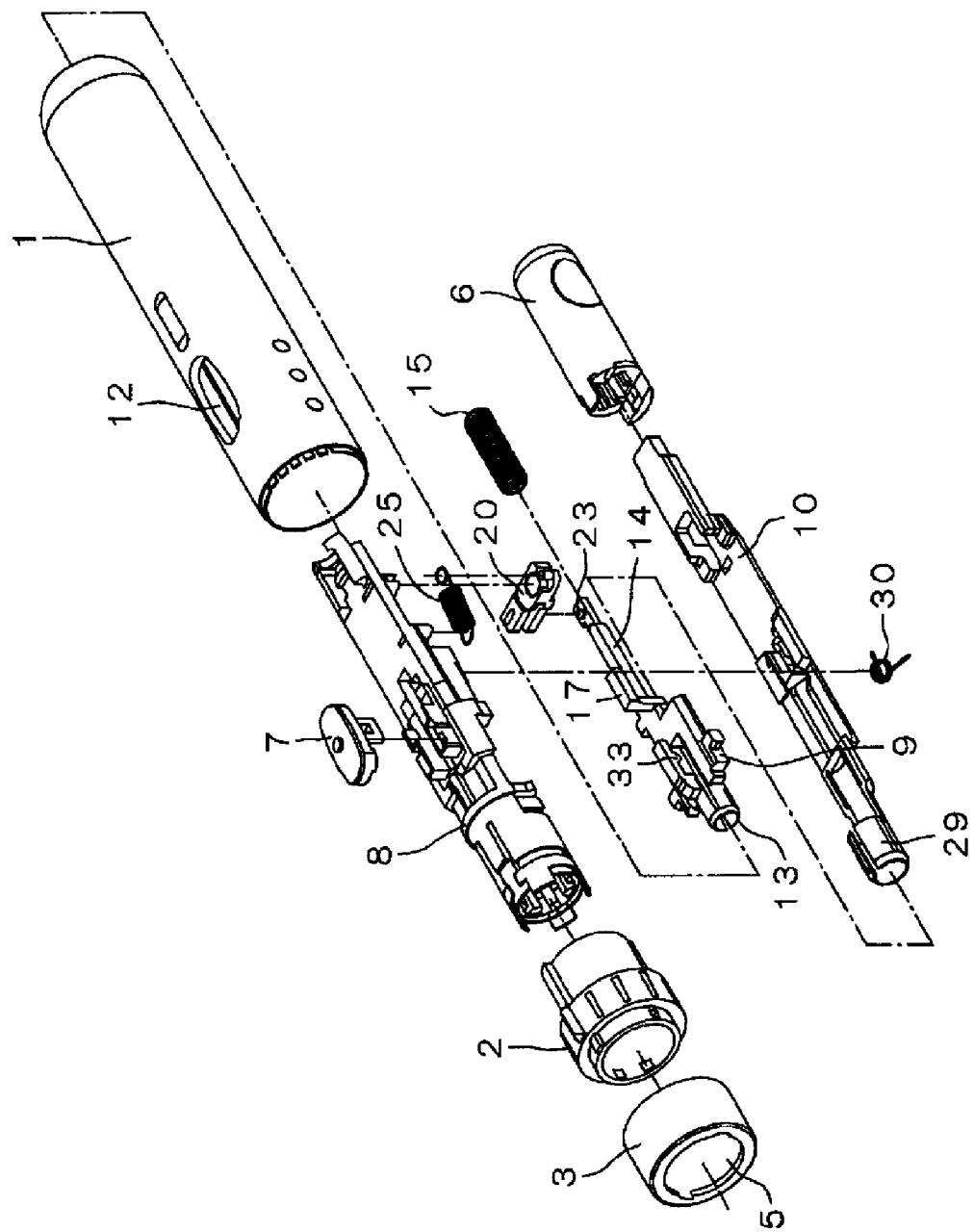
FIG. 2 is an exploded perspective view of the puncture instrument according to the embodiment of the invention.

To an upper end opening of the main body case 1 is attached an operation button 6 to eject the puncture needle 4, as is well known. A puncture button 7 for the puncture needle 4 is placed on the surface in the middle of the main body case 1. As shown in FIG. 2, a base member 8, a needle holder 9 slidably attached to this base member 8, and a puncture needle ejecting member 10 also slidably attached to this base member 8 are provided inside the main body case 1.

Figure 6A:
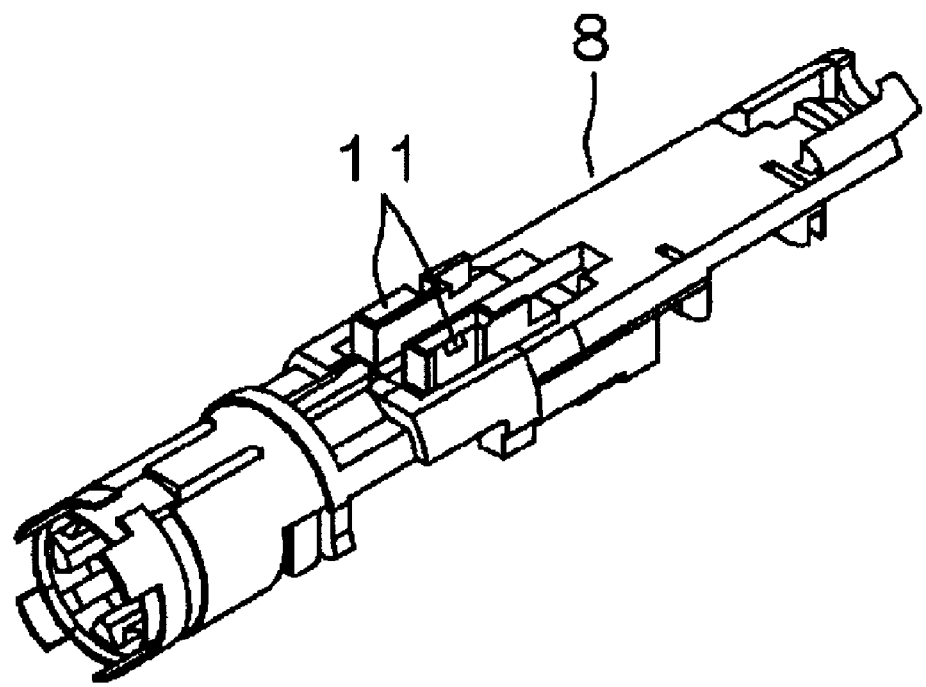
FIG. 6A is a top perspective view of a base member.
Figure 6B:
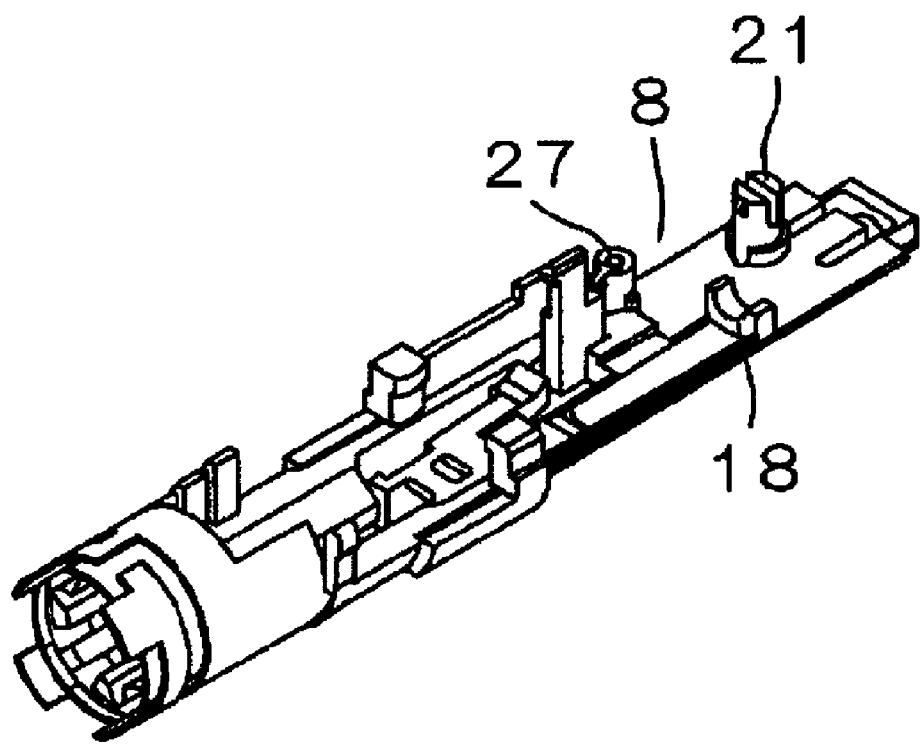
FIG. 6B is a bottom perspective view of the base member.
Figure 6C:
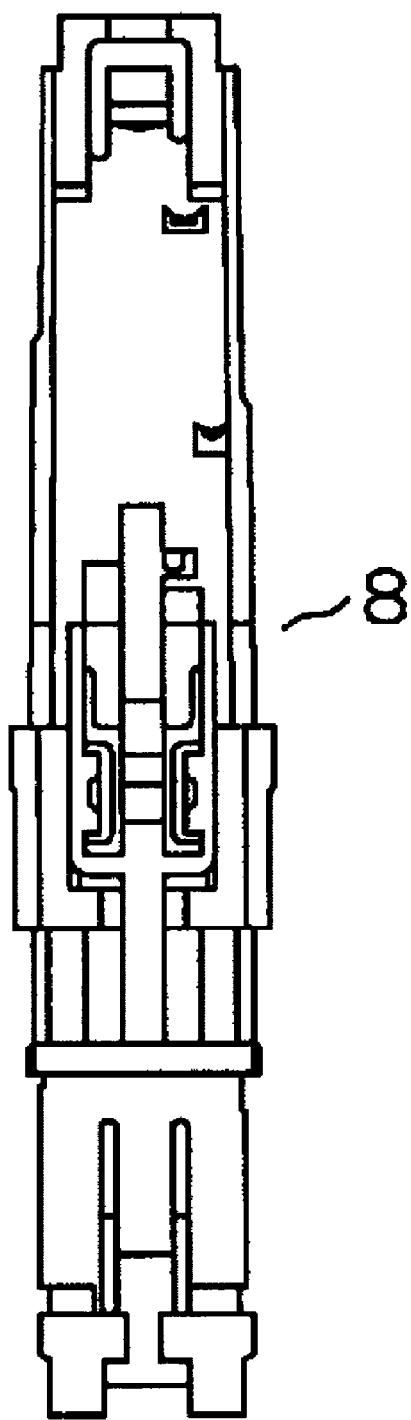
FIG. 6C is a top view of the base member.
Figure 6D:
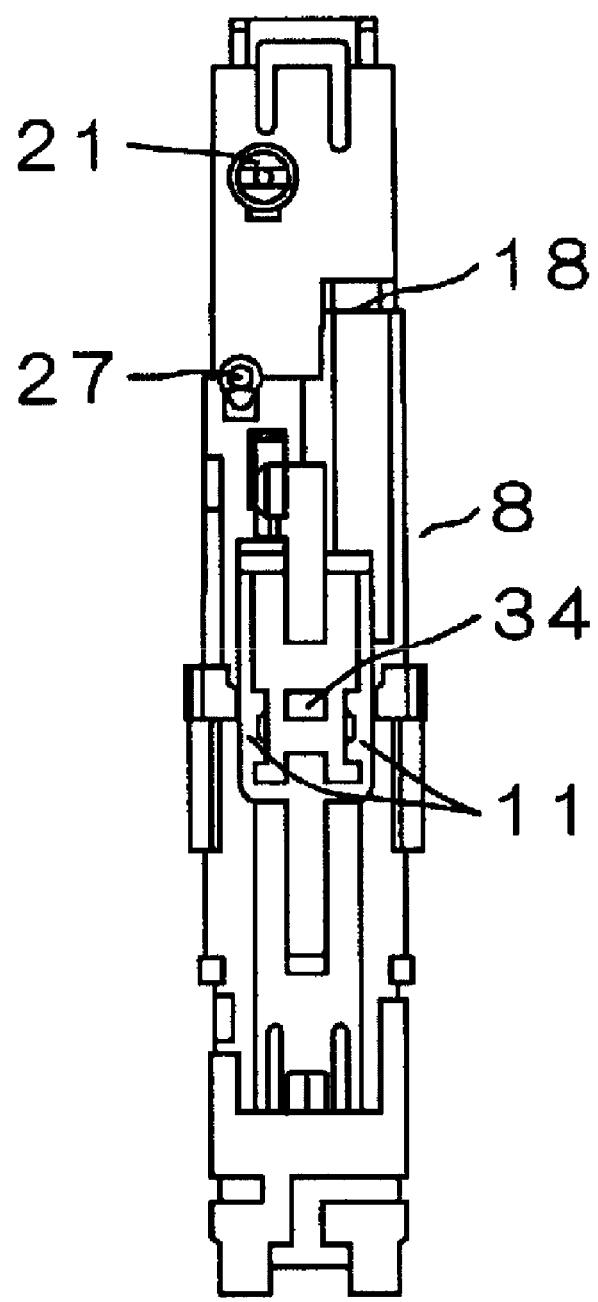
FIG. 6D is a bottom view of the base member.
Figure 6E:
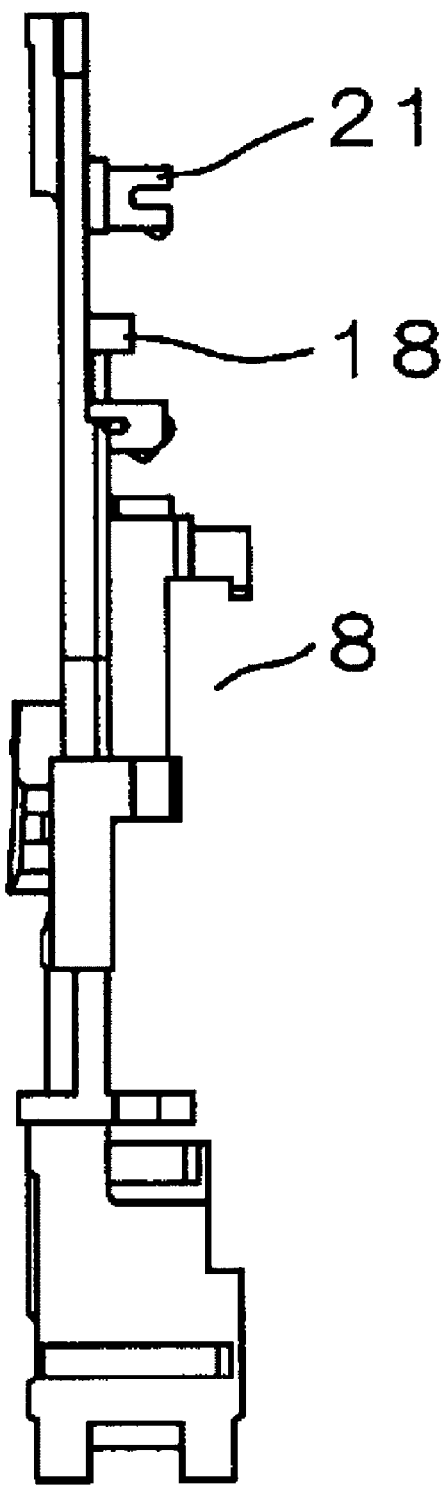
FIG. 6E is a side view of the base member viewed from one side.
Figure 6F:
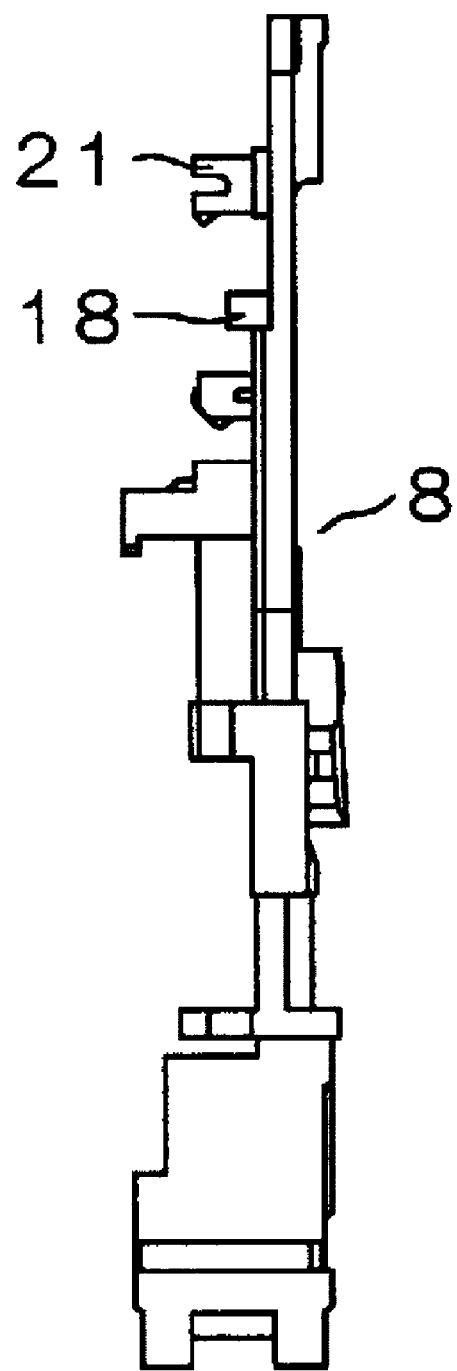
FIG. 6F is a side view of the base member viewed from the other side.

The base member 8 is configured as shown in FIGS. 6A through 6F. FIG. 6A is a top perspective view of the base member 8; FIG. 6B is a bottom perspective view of the base member 8; FIG. 6C is a top view of the base member 8; FIG. 6D is a bottom view of the base member 8; FIG. 6E is a side view of the base member 8 viewed from one side; and FIG. 6F is a side view of the base member 8 viewed from the other side.

The base member 8 is fixed inside the main body case 1. As described next in detail, the needle holder 9 and the puncture needle ejecting member 10 are slidably attached in relation to the fixed base member 8.

Outwardly protruding attachment portions 11 are provided on the top surface in the middle of the base member 8. The puncture button 7 is attached to these attachment portions 11 through an opening 12 of the main body case 1.

Figure 7A:
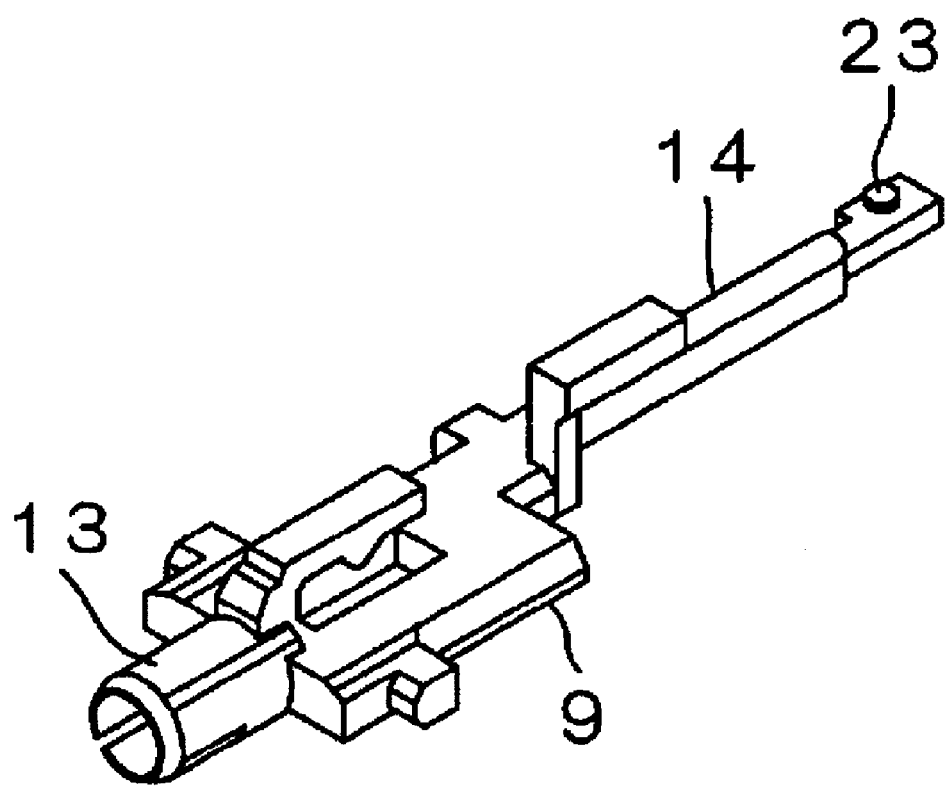
FIG. 7A is a top perspective view of a needle holder 9.
Figure 7B:
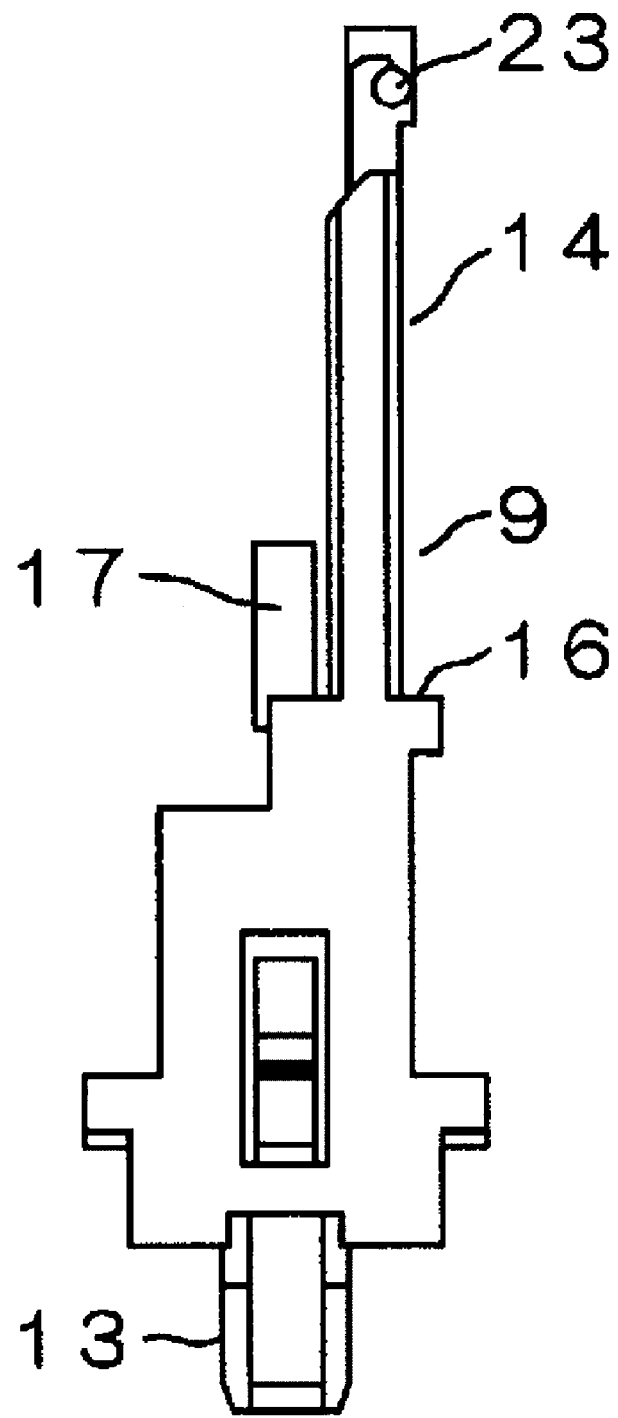
FIG. 7B is a bottom view of the needle holder.
Figure 7C:
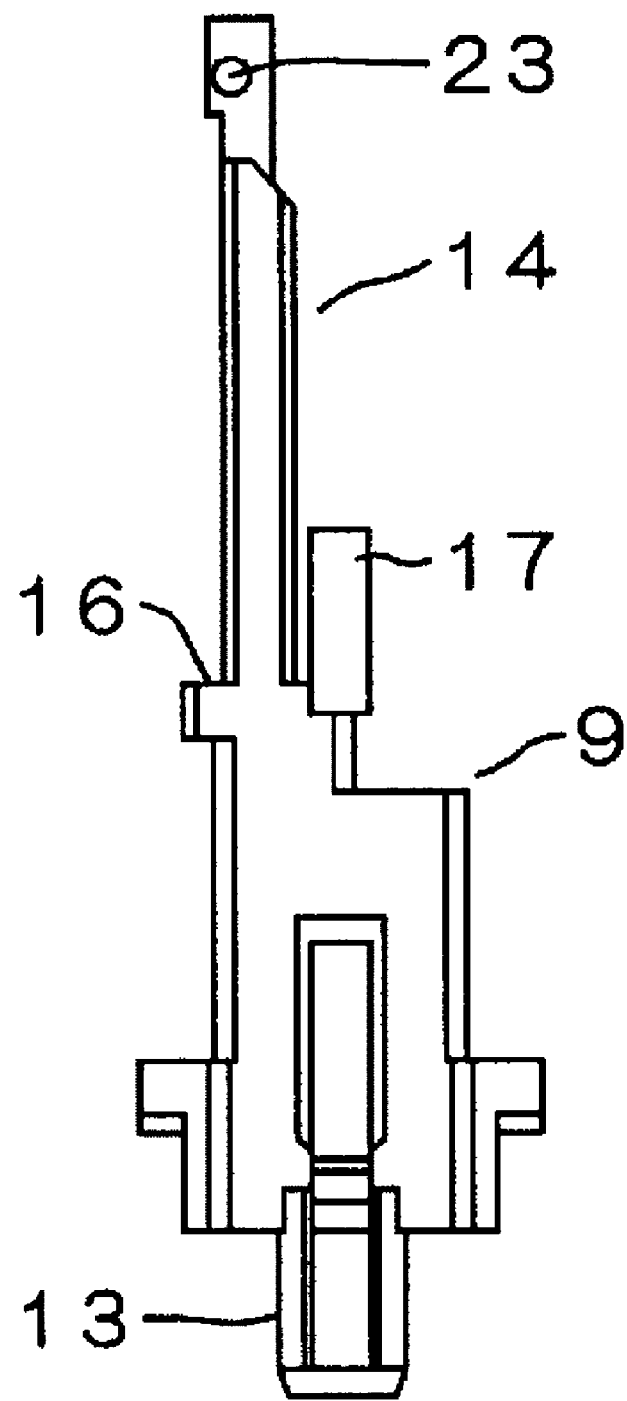
FIG. 7C is a top view of the needle holder.
Figure 7D:
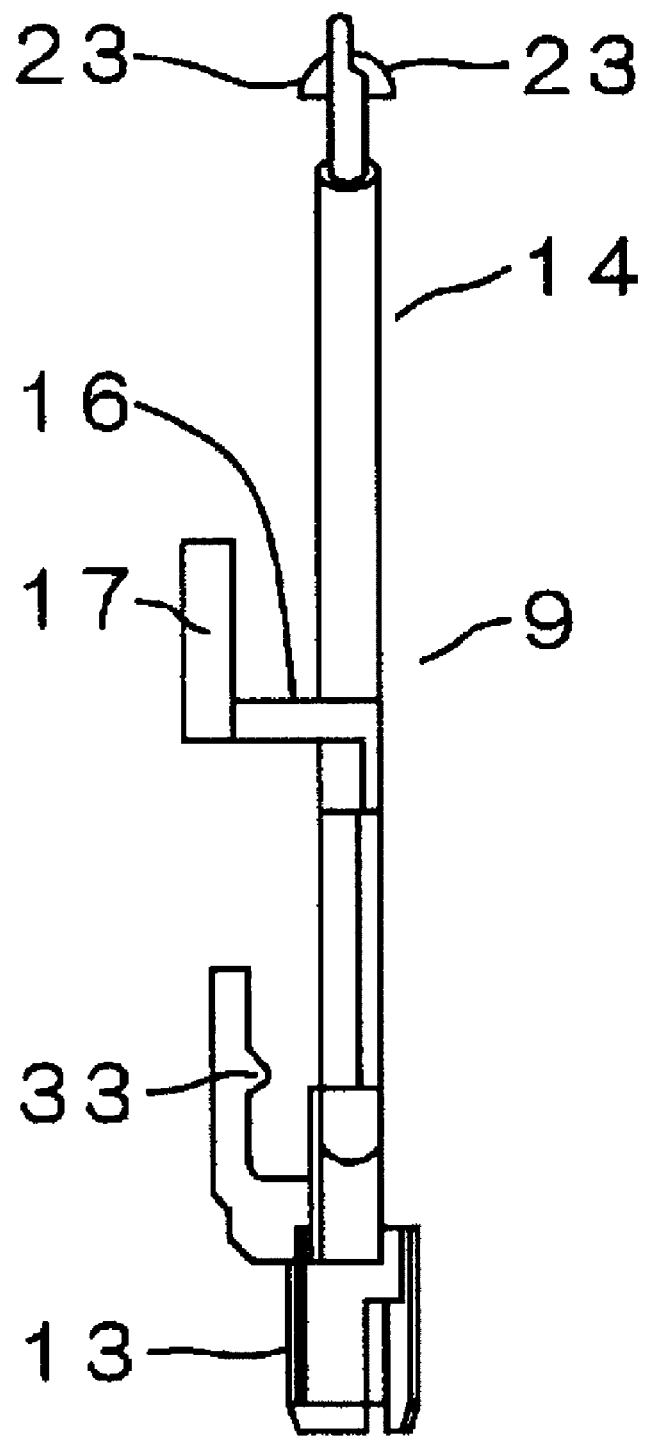
FIG. 7D is a side view of the needle holder viewed from one side.
Figure 7E:
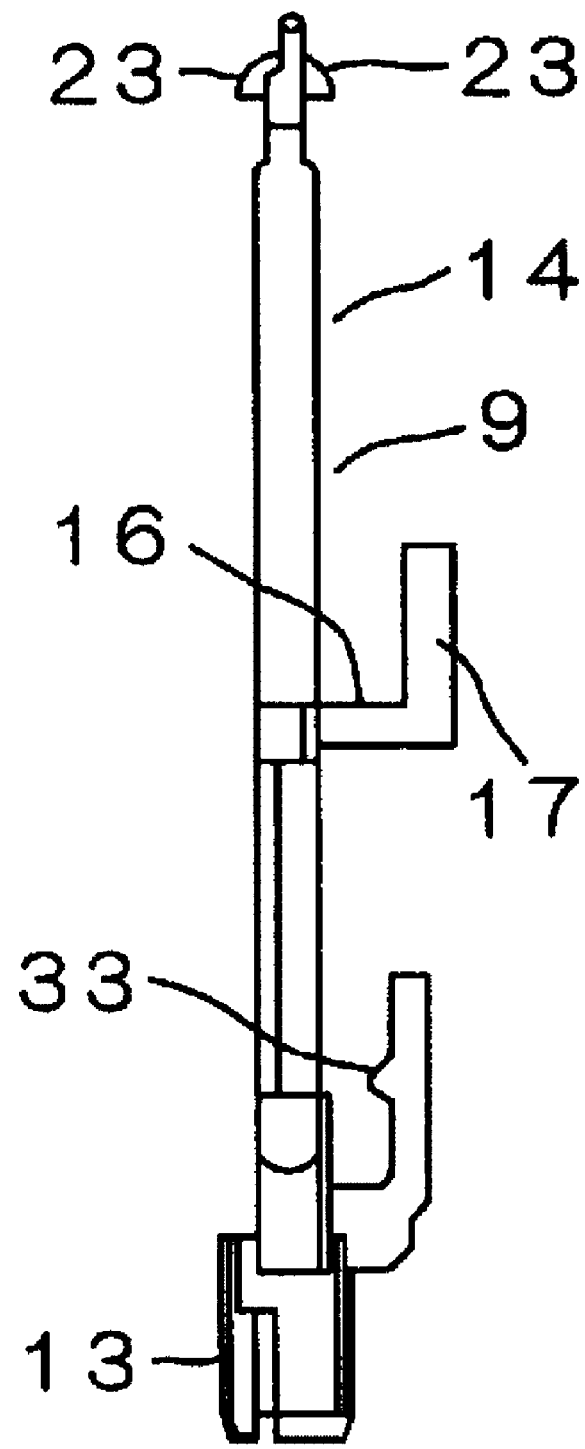
FIG. 7E is a side view of the needle holder viewed from the other side.

The needle holder 9 is configured as shown in FIGS. 7A through 7E. FIG. 7A is a top perspective view of a needle holder 9; FIG. 7B is a bottom view of the needle holder 9; FIG. 7C is a top view of the needle holder 9; FIG. 7D is a side view of the needle holder 9 viewed from one side; and FIG. 7E is a side view of the needle holder 9 viewed from the other side.

Figure 10:
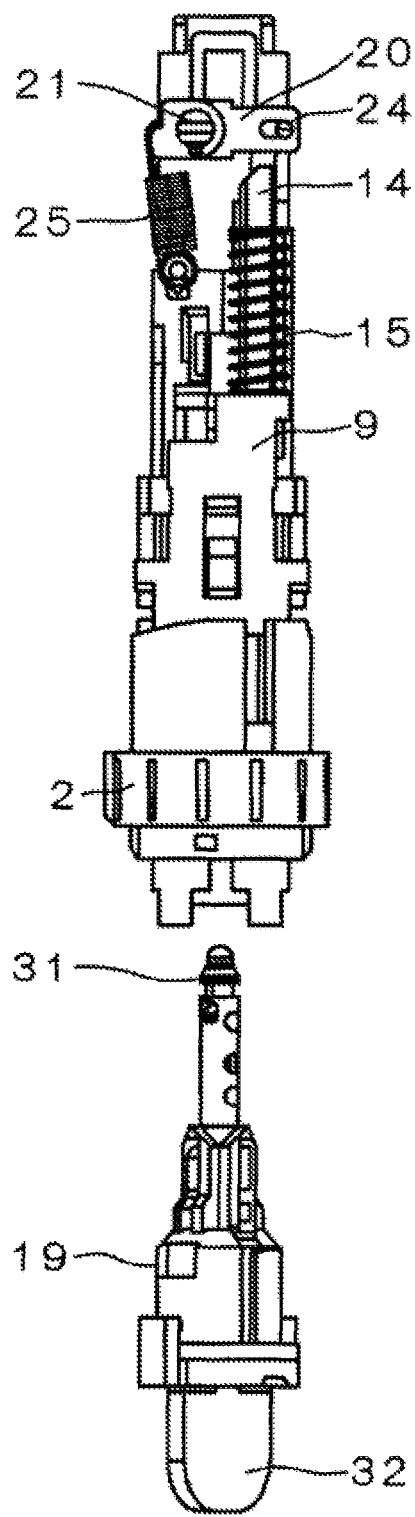
FIG. 10 illustrates a state of use of the puncture instrument according to the embodiment of the invention.

As shown in FIGS. 7 and 10, a needle holding portion 13 is provided on the lower end side of the needle holder 9. A rod-shaped coupling portion 14 is provided higher on the needle holder 9. A coil-shaped elastic object 15 shown in FIG. 2 is placed around the periphery of the rod-shaped coupling portion 14. The coil-shaped elastic object 15 is attached on the lower end side to an abutment surface 16 provided in the middle of the needle holder 9.

Figure 4:
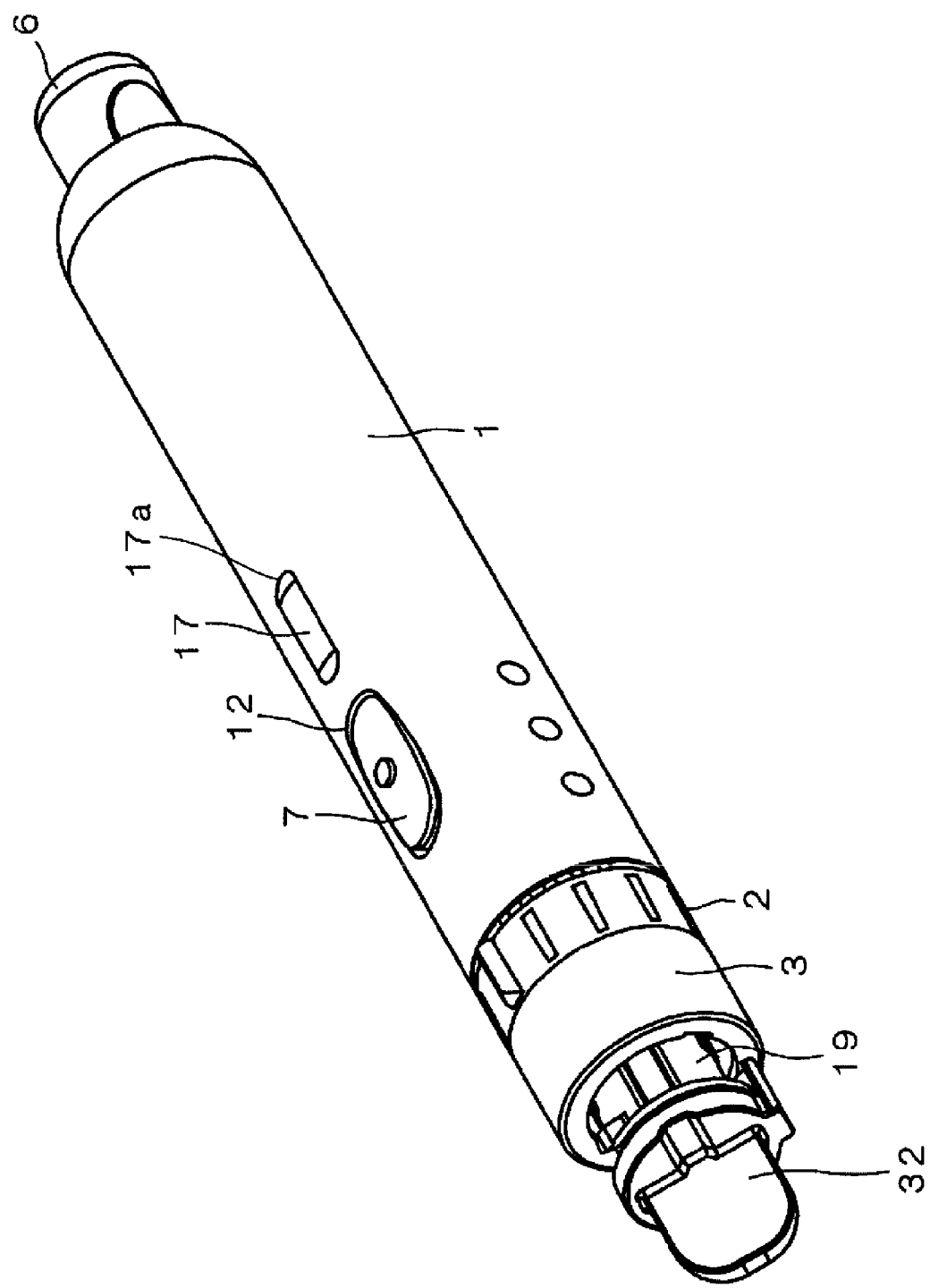
FIG. 4 is a perspective view illustrating a state of use of the puncture instrument according to the embodiment of the invention.

A protrusion 17, near the abutment surface 16, provided over the periphery of the elastic object 15 is to indicate a state where the needle holder 9 is ready for puncture, as shown in FIG. 4. The protrusion 17 is colored (e.g. green). When the protrusion 17 moves from the state shown in FIG. 10 toward the upper end side to the state shown in FIG. 4, the protrusion 17 appears in an indication window 17a provided in the periphery of the main body case 1, indicating to a user that the preparation for puncture is complete.

The elastic object 15 is attached on the upper end side to an abutment surface 18 provided on the upper end side of the base member 8 shown in FIG. 6B or the like. This means that the elastic object 15 is attached to the abutment surface 18 of the base member 8 and to the abutment surface 16 of the needle holder 9, and therefore the elastic object 15 is compressed when the needle holder 9 is moved to the upper end side, as shown in FIG. 11, and is then stretched when the needle holder 9 is moved to the lower end side, as shown in FIG. 13.

Figure 11:
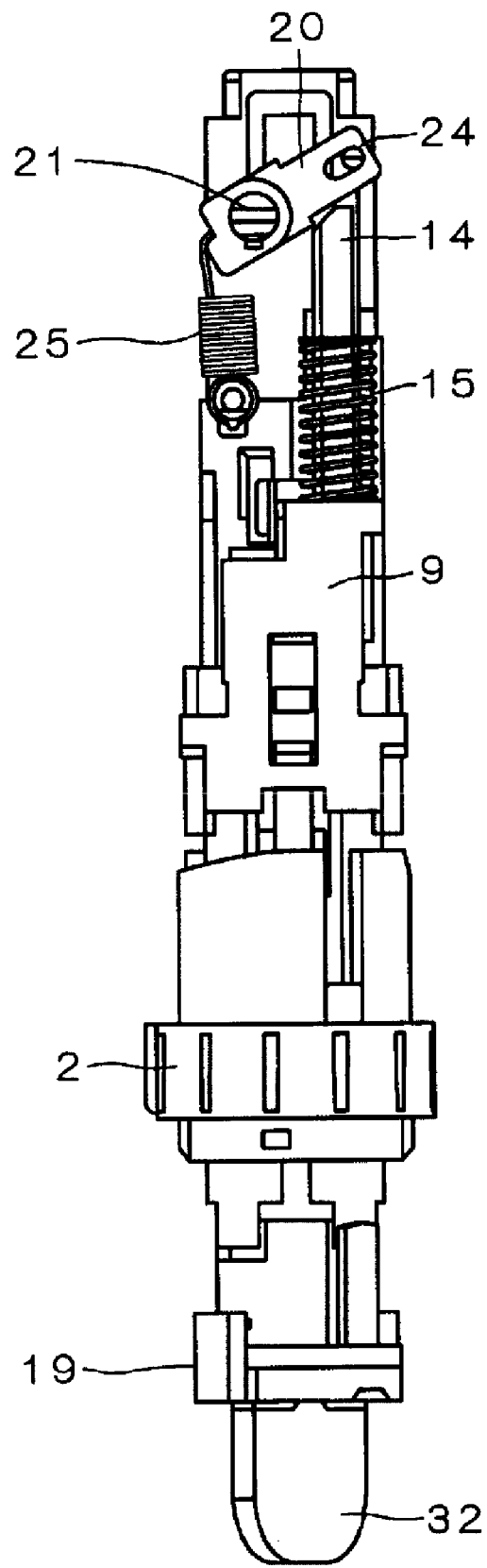
FIG. 11 illustrates a state of use of the puncture instrument according to the embodiment of the invention.
Figure 12:
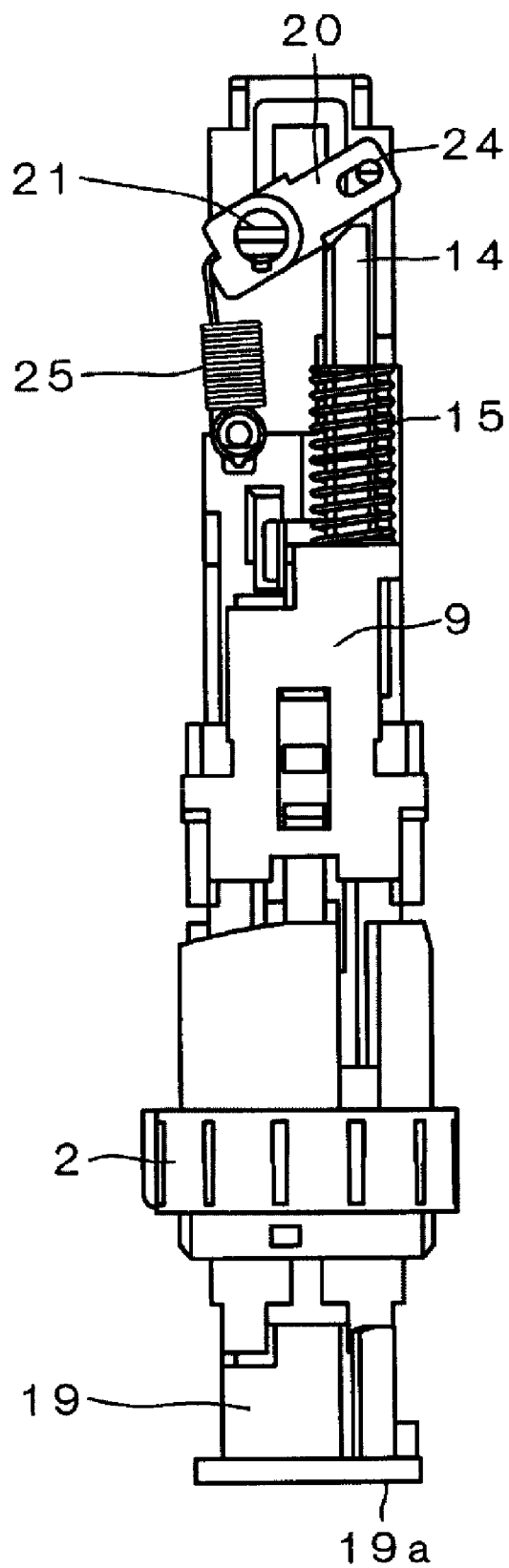
FIG. 12 illustrates a state of use of the puncture instrument according to the embodiment of the invention.
Figure 13:
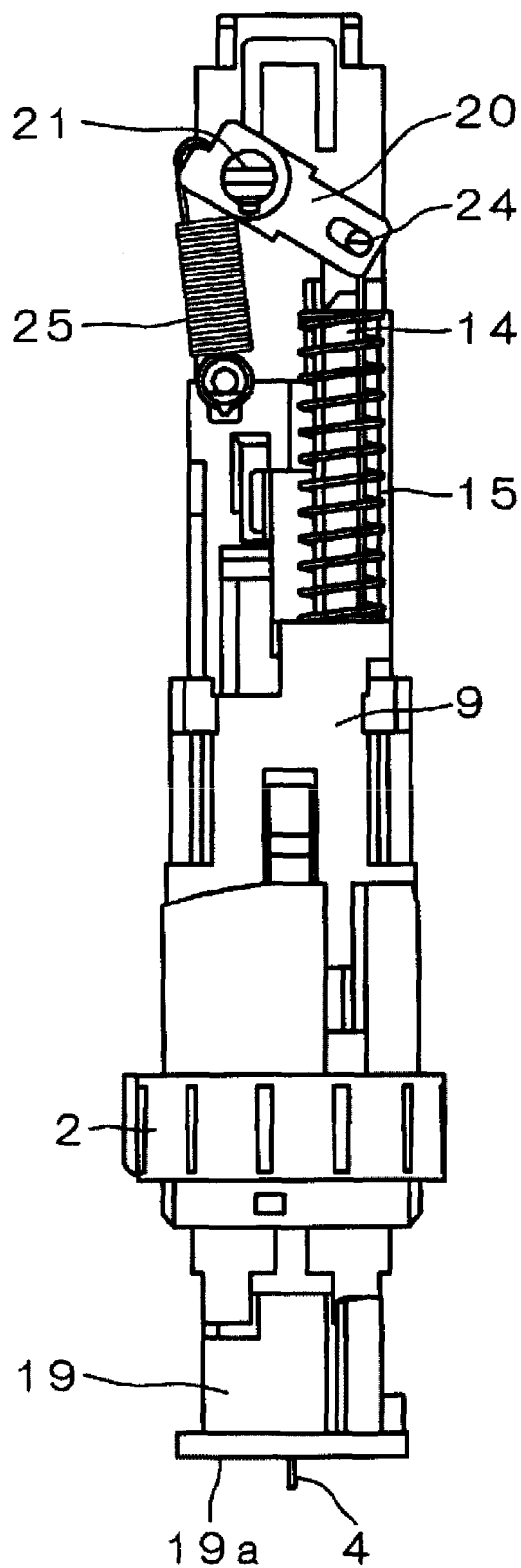
FIG. 13 illustrates a state of use of the puncture instrument according to the embodiment of the invention.

FIGS. 10 to 13 illustrate these operating states, which will be described later in detail, where FIG. 10 shows a state in which the puncture needle cartridge 19 is not yet attached to the needle holder 9, FIG. 11 shows a state in which the puncture needle cartridge 19 is being attached to the needle holder 9, FIG. 12 shows a state in which the puncture needle cartridge 19 is already attached to the needle holder 9, and FIG. 13 shows a state in which the puncture operation is performed with the puncture needle cartridge 19 being attached to the needle holder 9.

As will be understood also from FIGS. 10 through 13, the coupling portion 14 of the needle holder 9 is coupled on the upper end side to a rotator 20. Specifically, the rotator 20 is shaped into a board which extends in a direction perpendicular to the vertical direction of the main body case 1 in the state where the puncture needle 4 is not yet attached (see FIG. 10), and is pivotally supported at the center by a rotation shaft 21 provided on the upper end side of the base member 8.

Figure 9A:
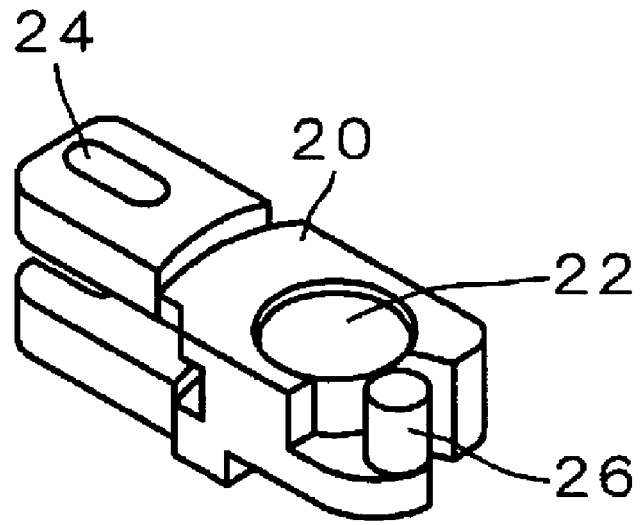
FIG. 9A is a perspective view of a rotator.
Figure 9B:
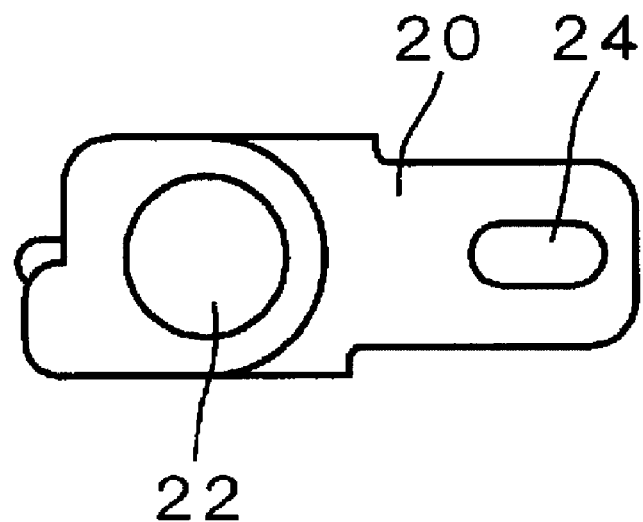
FIG. 9B is a top view of the rotator.
Figure 9C:
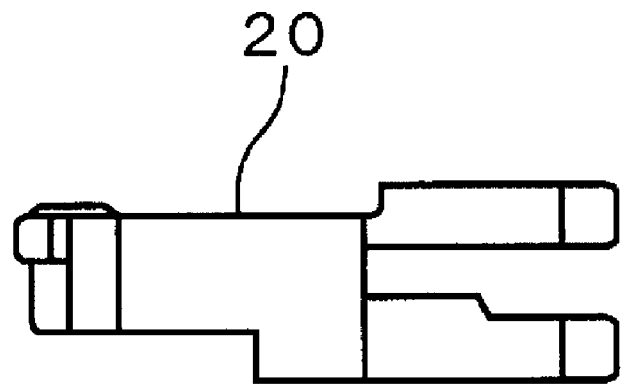
FIG. 9C is a side view of the rotator viewed from one side.

The rotator 20 is configured as shown in FIGS. 9A through 9C. FIG. 9A shows a perspective view of the rotator 20; FIG. 9B shows a top view of the rotator 20; and FIG. 9C shows a side view of the rotator 20 viewed from one side. As is clear from FIGS. 9A through 9C, in the middle of the rotator 20 is formed a through hole 22 through which the rotation shaft 21 enters. On the right side of the through hole 22 are formed slot-shaped through holes 24 into which protrusions 23 formed on the upper end side of the coupling portion 14 of the needle holder 9 (see FIGS. 7A to 7E) fit, and on the left side of the through hole 22 is formed an engagement portion 26 with which a coil-shaped elastic object 25 (see FIGS. 10 to 13) engages on the upper side. The through holes 24 are provided at two positions in a manner that they overlap with each other on the front and back sides, as will be understood from FIG. 9. The above-described protrusions 23 on the front and back sides shown in FIGS. 7A to 7E fit into the two through holes 24.

The elastic objects 15 and 25 are provided below the rotator 20 on the lower end side of the main body case 1. The lower end of the elastic object 25 is attached to a protrusion 27 shown in FIGS. 6B and 6D.

Figure 8A:
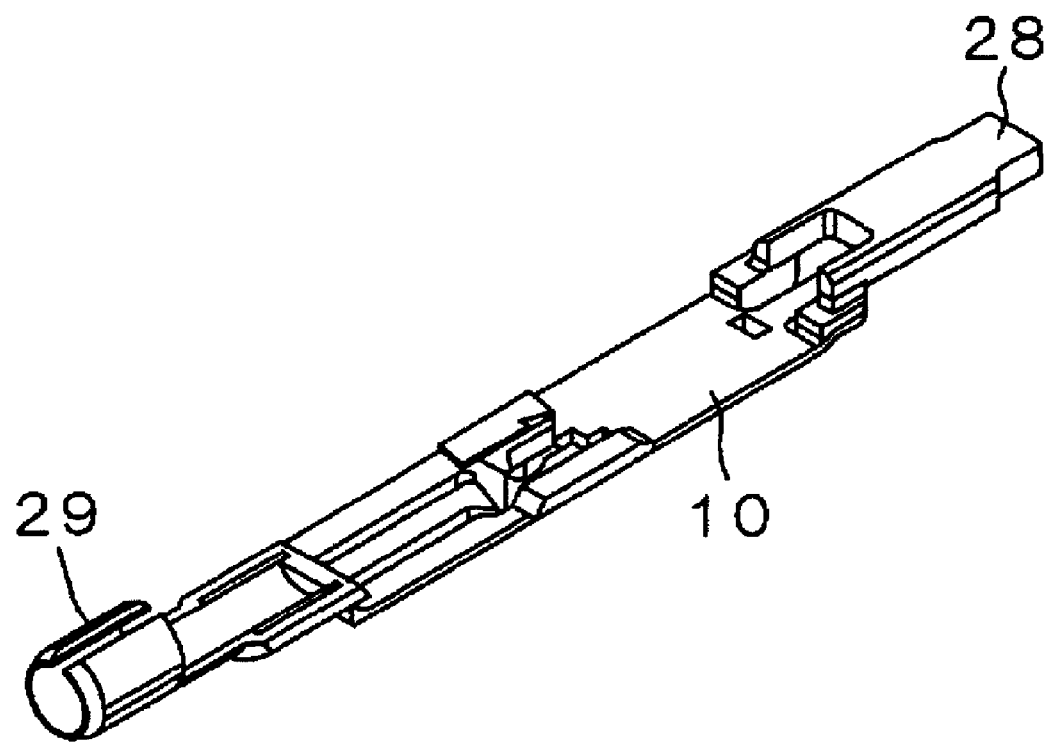
FIG. 8A is a top perspective view of a puncture needle ejecting member.
Figure 8B:
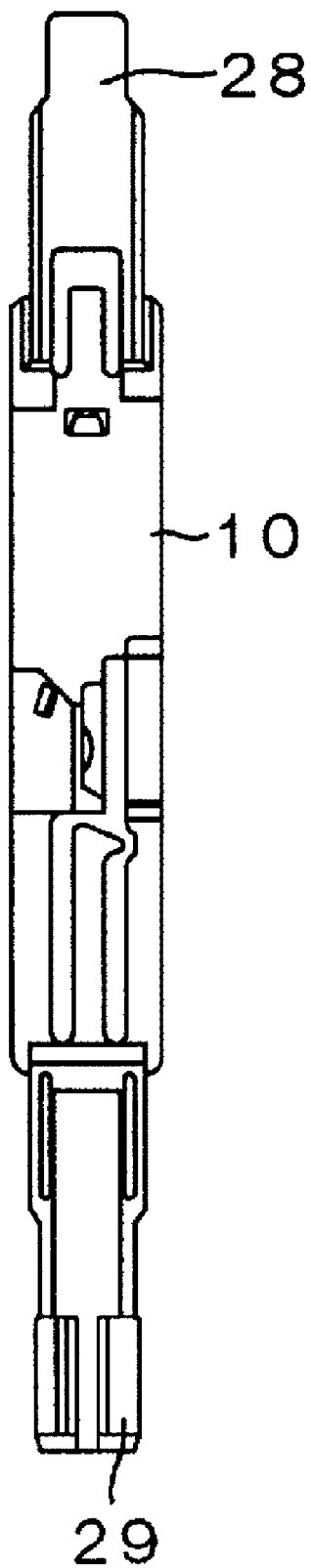
FIG. 8B is a top view of the puncture needle ejecting member.
Figure 8C:
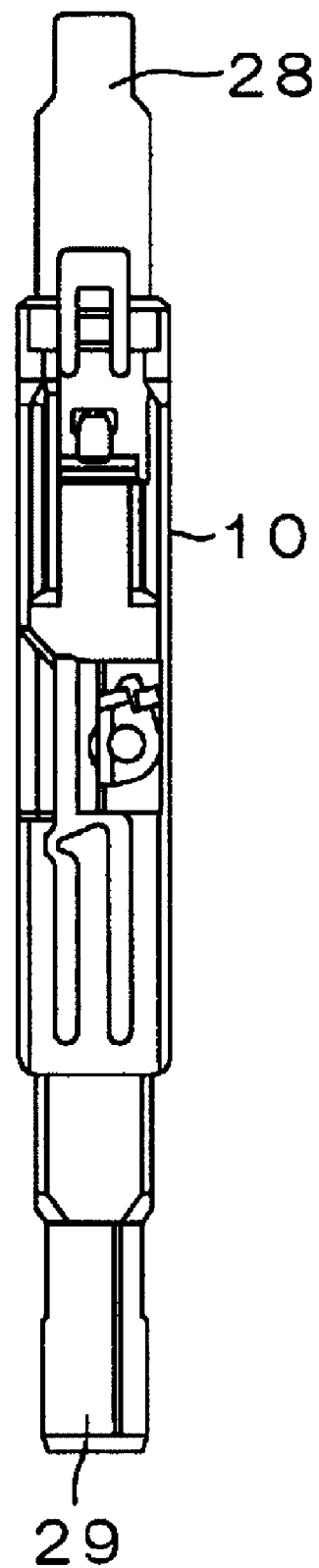
FIG. 8C is a bottom view of the puncture needle ejecting member.
Figure 8D:
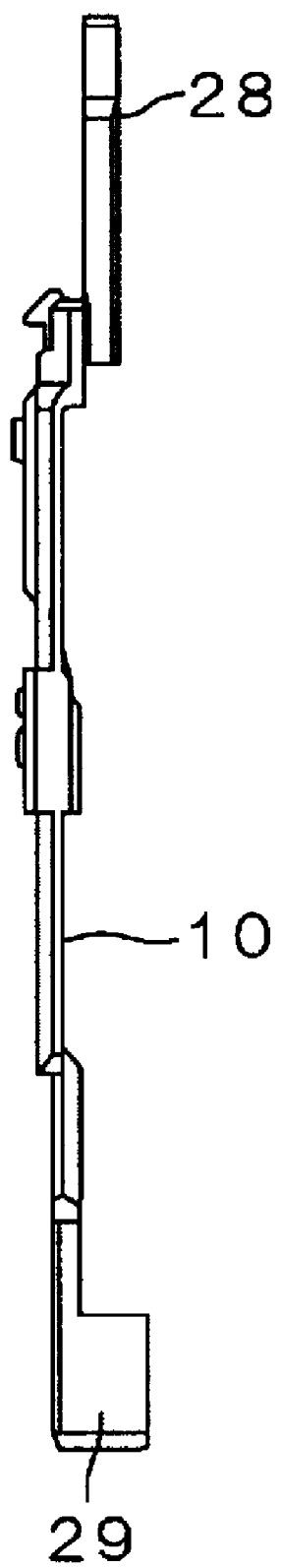
FIG. 8D is a side view of the puncture needle ejecting member viewed from one side.
Figure 8E:
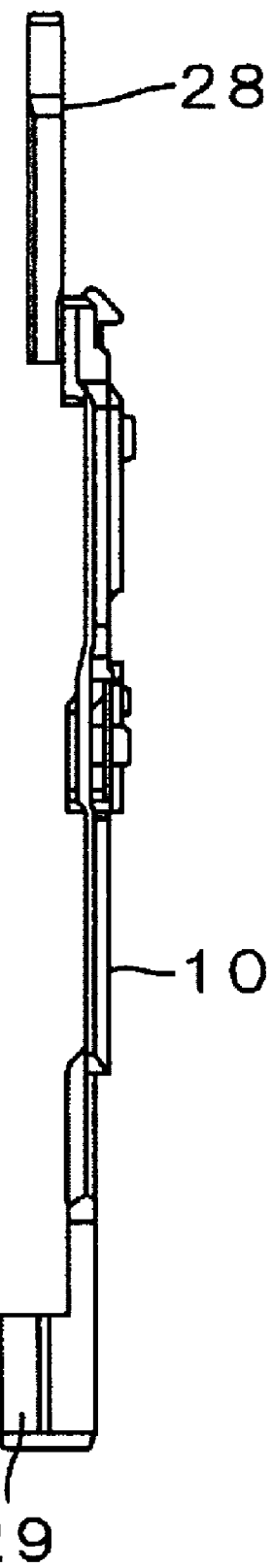
FIG. 8E is a side view of the puncture needle ejecting member viewed from the other side.

The puncture needle ejecting member 10 vertically slidably attached in relation to the base member 8 is configured as shown in FIGS. 8A through 8E. FIG. 8A is a top perspective view of the puncture needle ejecting member 10; FIG. 8B is a top view of the puncture needle ejecting member 10; FIG. 8C is a bottom view of the puncture needle ejecting member 10; FIG. 8D is a side view of the puncture needle ejecting member 10 viewed from one side; and FIG. 8E is a side view of the puncture needle ejecting member 10 viewed from the other side.

An attachment portion 28 to which the operation button 6 for ejecting the puncture needle cartridge 19 is attached is provided on the upper end side of the puncture needle ejecting member 10, as is well known. A pressing portion 29 for ejecting the puncture needle cartridge 19 is provided on the lower end of the puncture needle ejecting member 10. A torsion spring 30 for biasing the operation button 6 upward (see FIG. 2) is attached in the middle of the puncture needle ejecting member 10.

Figure 3:
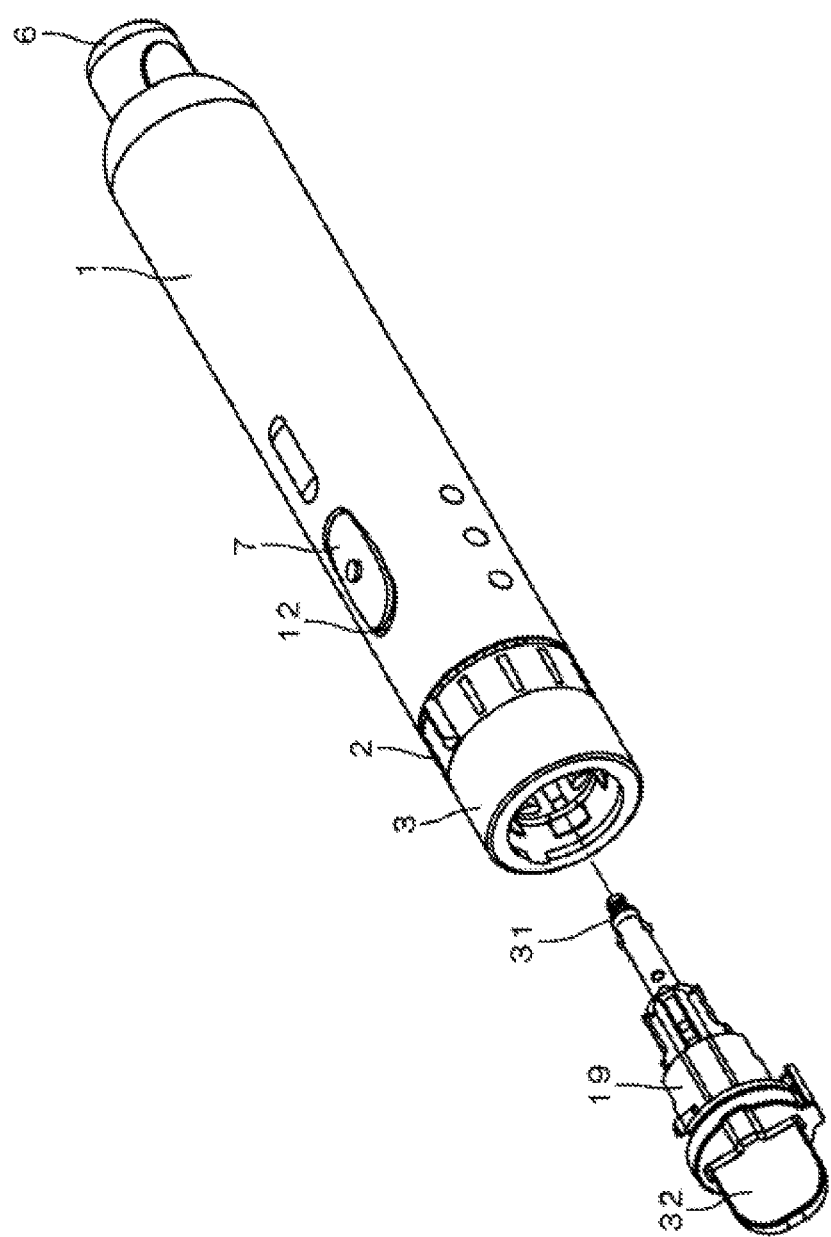
FIG. 3 is a perspective view illustrating a state of use of the puncture instrument according to the embodiment of the invention.
Figure 5:
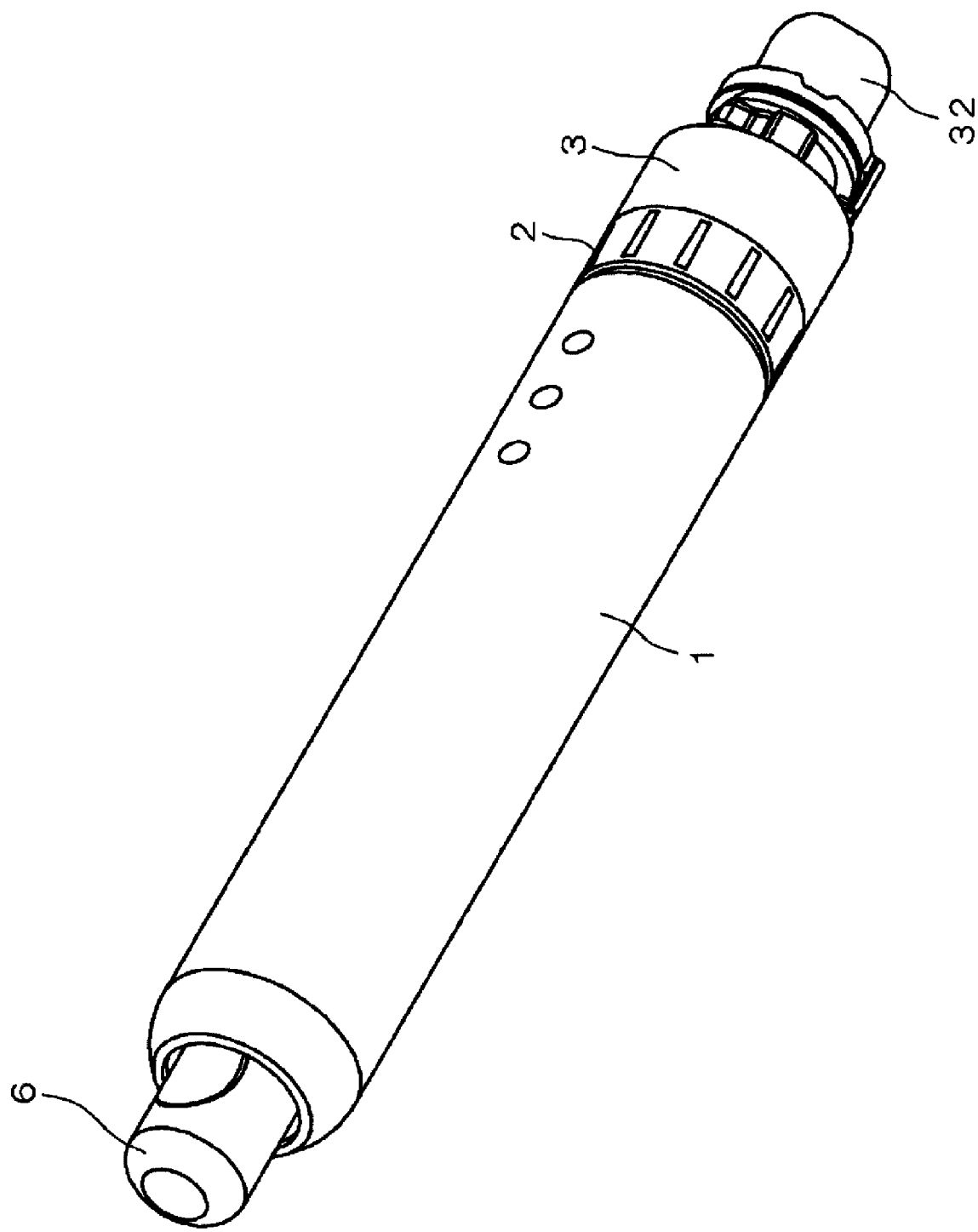
FIG. 5 is a perspective view illustrating a state of use of the puncture instrument according to the embodiment of the invention.

In reference to the above-described configuration, FIGS. 3 and 10 show a state in which the puncture needle cartridge 19 is not yet attached to the main body case 1, and FIGS. 4, 5, and 11 show a state in which the puncture needle cartridge 19 is being attached to the main body case 1.

As will be understood from FIG. 11, the insertion of the puncture needle cartridge 19 through the puncture aperture 5 at the lower end of the main body case 1 causes a gripping portion 31 of the puncture needle cartridge 19 to be inserted into the needle holding portion 13 on the lower end side of the needle holder 9 shown in FIG. 2, and moves the needle holder 9 upward. This upward movement of the needle holder 9, as shown in FIG. 11, causes the rotator 20 to be pushed up on the side of the elastic object 15 by the coupling portion 14 of the needle holder 9. In this state, a protection cap 32 on the front end side of the puncture needle cartridge 19 is twisted off, so that the state shown in FIG. 12 is realized. In the state shown in FIG. 12, a locking protrusion 33 provided on the needle holder 9 engages with a locking hole 34 provided between the attachment portions 11 of the base member 8 shown in FIG. 6D and, as a result, the needle holder 9 is held in an upper position as shown in FIG. 12. The elastic object 15 is then compressed as shown in FIG. 12 along with the upward movement of the needle holder 9.

In this state, a user brings a skin abutment portion 19a of the puncture needle cartridge 19 shown in FIG. 12 into contact with the skin, and then pushes the puncture button 7. Upon the puncture button 7 being pushed, the locking hole 34 is pushed to the puncture needle ejecting member 10 side, resulting in releasing the lock between the locking protrusion 33 and the locking hole 34, and the state becomes the one shown in FIG. 13.

That is, the compressed elastic object 15 extends, thereby thrusting the needle holder 9 to the bottom end side and, as a result, the puncture needle 4 sticks out from the skin abutment portion 19a to the skin side to puncture, as shown in FIG. 13.

The next moment, the tension of the elastic object 25 applied to the rotator 20 on the side opposite to the through hole 24 causes the puncture needle 4 to return into the main body case 1 (the rotator 20 becomes almost the same state as in FIG. 10). The tension of the elastic object 25 then prevents the puncture needle 4 from sticking out outside the skin abutment portion 19a again.

The puncture instrument of the embodiment is provided with the elastic object 25 for pulling the needle holder 9, moved to the skin abutment portion 19a (the puncture aperture 5) side by the elastic object 15, back to the upper end side inside the main body case 1, where the rotator 20 which rotates around the rotation shaft 21 is provided above the needle holding portion 13 of the needle holder 9 inside the main body case 1. The rotator 20 is coupled with the coupling portion 14 of the needle holder 9 on one side of the rotator 20 and is coupled with the elastic object 25 on the other side of the rotator 20, and the rotation shaft 21 for the rotator 20 is fixed to the main body case 1. Note here that the rotation shaft 21 for the rotator 20 is fixed to the base member 8, which is fixed to the main body case 1, and therefore the rotation shaft 21 for the rotator 20 is fixed to the main body case 1.

For this reason, the repeated protrusion of the puncture needle 4 is prevented by the rotation of the rotator 20, which means that no impact sound is created unlike those which are provided with a conventional impact wall. As a result, the generation of an abnormal sound during puncture can be inhibited.

The embodiment can also prevent the repeated protrusion of the tip of the puncture needle 4. Specifically, in FIG. 13, the tip of the puncture needle 4 is protruded from the puncture aperture 5 of the main body case 1 as described above. Since the elastic object 25 is then stretched, the next moment the elastic object 25 contracts to its original state, causing the needle holder 9 to be pulled up, and the tip of the puncture needle 4 is returned into the puncture aperture 5 of the main body case 1.

At this moment, the tension of the elastic object 25 is larger than the force of the elastic object 15 to protrude the tip of the puncture needle 4 again outside the puncture aperture 5 of the main body case 1 via the puncture needle cartridge 19, and therefore allows the repeated protrusion of the tip of the puncture needle 4 to be prevented.

While there have been described what are at present considered to be a preferred embodiment of the invention, various modifications and variations may be made thereto, and it is intended that appended claims cover all such modifications and variations as fall within the true spirit and scope of the invention.

INDUSTRIAL APPLICABILITY

As stated above, the invention is provided with the second elastic object for pulling the needle holder, moved to the puncture aperture side by the first elastic object, back to the upper end side inside the main body case, where the rotator which rotates around the rotation shaft fixed to the main body case is provided above the needle holding portion of the needle holder inside the main body case, and where the rotator is coupled with the coupling portion of the needle holder on one of both sides of the rotator with the rotation shaft interposed therebetween and is coupled with the second elastic object on the other side. The repeated protrusion of the puncture needle is therefore prevented by the rotation of the rotator, which means that no impact sound is created unlike those which are provided with a conventional impact wall. As a result, the generation of an abnormal sound during puncture can be inhibited.

DESCRIPTION OF THE SYMBOLS

1: Main body case
2: Puncture depth adjustment ring
3: Front-end ring

4: Puncture needle
5: Puncture aperture
6: Operation button
7: Puncture button
8: Base member
9: Needle holder
10: Puncture needle ejecting member
11: Attachment portion
12: Opening
13: Needle holding portion
14: Coupling portion
15: Elastic object
16: Abutment surface
17: Protrusion
17a: Indication window
18: Abutment surface
19: Puncture needle cartridge
19a: Skin abutment portion
20: Rotator
21: Rotation shaft
22: Through hole
23: Protrusion
24: Through hole
25: Elastic object
26: Engagement portion
27: Protrusion
28: Attachment portion
29: Pressing portion
30: Torsion spring
31: Gripping portion
32: Protection cap
33: Locking protrusion
34: Locking hole

The invention claimed is:

1. A puncture instrument comprising: a cylindrical main body case having a puncture aperture on a lower end side of the cylindrical main body case; a needle holder provided on a puncture aperture side inside the cylindrical main body case, the needle holder having a coupling portion; a first elastic object for moving the needle holder to the puncture aperture side; and a second elastic object for pulling the needle holder back to an upper end side of the cylindrical main body case, from a state in which the needle holder is moved to the puncture aperture side by the first elastic object, wherein a rotator is configured to rotate around a rotation shaft fixed to the cylindrical main body case and is provided above a needle holding portion of the needle holder inside the cylindrical main body case, and wherein the rotator is coupled with the coupling portion on a first one of two sides of the rotator with the rotation shaft interposed therebetween and is coupled with the second elastic object on a second one of the two sides of the rotator, and wherein a protrusion is formed on the coupling portion and a hole is formed in the rotator, and the protrusion is configured to fit into the hole so as to couple the rotator with the coupling portion.

2. The puncture instrument according to claim 1, wherein: the needle holding portion is on a lower end side of the needle holder and the coupling portion is rod-shaped and is on an upper end side of the needle holder, the first elastic object is coil-shaped, and the first elastic object is placed around a periphery of the rod shaped coupling portion, and the first elastic object is attached to the needle holder on the lower end side of the needle holder and is attached to the cylindrical main body case on the upper end side of the cylindrical main body case.

3. The puncture instrument according to claim 1, wherein a base member is fixed inside the cylindrical main body case, and the needle holder is longitudinally slidably mounted in relation to the base member.

4. The puncture instrument according to claim 2, wherein a base member is fixed inside the cylindrical main body case, and the needle holder is longitudinally slidably mounted in relation to the base member.

5. The puncture instrument according to claim 3, wherein the first elastic object is attached to the base member on an upper end side of the base member.

6. The puncture instrument according to claim 4, wherein the first elastic object is attached to base member on an upper end side of the base member.

7. The puncture instrument according to claim 3, wherein the rotation shaft for the rotator is provided on the base member.

8. The puncture instrument according to claim 4, wherein the rotation shaft for the rotator is provided on the base member.

9. The puncture instrument according to claim 5, wherein the rotation shaft for the rotator is provided on the base member.

10. The puncture instrument according to claim 6, wherein the rotation shaft for the rotator is provided on the base member.

11. The puncture instrument according to claim 1, wherein the rotator is board-shaped and extends in a direction perpendicular to a longitudinal direction of the cylindrical main body case in a state in which a puncture needle is not attached, and the first elastic object and the second elastic object are disposed below the rotator on the lower end side of the cylindrical main body case.

12. The puncture instrument according to claim 1, wherein the rotator is directly coupled with the coupling portion.

13. The puncture instrument according to claim 1, wherein the first elastic object and the second elastic object are in between the needle holder and the rotator.

14. The puncture instrument according to claim 1, wherein at least a portion of the needle holder is closer to the puncture aperture than the first elastic object.

15. The puncture instrument according to claim 1, wherein a longitudinal axis of the first elastic object and a longitudinal axis of the second elastic object are disposed along a longitudinal direction of the puncture instrument.

* * * * *